(12) United States Patent
Lambertson

(10) Patent No.: US 11,747,377 B2
(45) Date of Patent: Sep. 5, 2023

(54) METHOD FOR DETERMINING THE SYSTEM RESISTANCE OF A HANDHELD MEDICAL DEVICE

(71) Applicant: Roche Diagnostics Operations, Inc., Indianapolis, IN (US)

(72) Inventor: Michael Lambertson, Mannheim (DE)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 0 days.

(21) Appl. No.: 17/075,303

(22) Filed: Oct. 20, 2020

(65) Prior Publication Data

US 2021/0055336 A1     Feb. 25, 2021

Related U.S. Application Data

(63) Continuation of application No. PCT/EP2019/060276, filed on Apr. 23, 2019.

(30) Foreign Application Priority Data

Apr. 24, 2018  (EP) .................................... 18168884

(51) Int. Cl.
  *G01R 27/14*   (2006.01)
  *G01R 31/36*   (2020.01)

(52) U.S. Cl.
  CPC ......... *G01R 27/14* (2013.01); *G01R 31/3648* (2013.01)

(58) Field of Classification Search
  CPC ........ G01R 27/14; G01R 27/00; G01R 27/02; G01R 27/10; G01R 29/02; G01R 31/3648;
  (Continued)

(56) References Cited

U.S. PATENT DOCUMENTS

2004/0128089 A1* 7/2004 Barsoukov ........... G01R 31/389
                                                                       702/65
2012/0025613 A1     2/2012 Morita et al.
(Continued)

FOREIGN PATENT DOCUMENTS

CN         1975444        6/2007
CN       101685117        3/2010
(Continued)

OTHER PUBLICATIONS

Jerry Chen HL Lin Childs Chung. Understanding Power MOSFET Parameters, Taiwan Semiconductor, A1611. 2016. (Year: 2016).*
(Continued)

*Primary Examiner* — Daniel R Miller
*Assistant Examiner* — Eric Sebastian Von Wald
(74) *Attorney, Agent, or Firm* — Woodard, Emhardt, Henry, Reeves & Wagner, LLP

(57) ABSTRACT

A method for determining system resistance of at least one power supply of a handheld medical device, the method including: a) generating at least one excitation voltage signal, wherein the excitation voltage signal comprises at least one direct current (DC) voltage signal, wherein the excitation voltage signal has a fast transition DC flank of 20 ns or less; b) applying the excitation voltage signal to at least one reference resistor having a predetermined or pre-defined resistance value, wherein the reference resistor is arranged in series with the power supply; c) measuring a response signal of the power supply; d) determining a signal flank from the response signal and determining an ohmic signal portion from one or both of shape and height of the signal flank; and e) determining the system resistance of the power supply from the ohmic signal portion.

18 Claims, 8 Drawing Sheets

(58) Field of Classification Search
CPC ...... G01R 31/36; G01R 31/364; G01R 23/10; G01R 33/32; G01R 19/16571; G01N 33/48785; G04F 1/005; G04F 5/00; G04F 10/00; G04F 10/04; H03M 1/109; H02J 7/18; H02P 9/16; H03K 2005/00293; H03K 2005/00013; H03K 3/00; H03K 5/125; H03K 5/1532; H03K 5/19; H04B 17/409; B06B 1/023
See application file for complete search history.

(56) References Cited

U.S. PATENT DOCUMENTS

| | | | |
|---|---|---|---|
| 2012/0100601 A1* | 4/2012 | Simmons | G01N 27/3272 435/287.7 |
| 2015/0164391 A1 | 6/2015 | Hernandez-Rosas et al. | |
| 2015/0280476 A1* | 10/2015 | Osswald | H02J 7/0029 324/426 |
| 2019/0170802 A1* | 6/2019 | Ling | G01R 31/52 |
| 2020/0014220 A1* | 1/2020 | Srinivasan | H02J 7/0029 |
| 2020/0083572 A1* | 3/2020 | Wang | H01M 10/4285 |

FOREIGN PATENT DOCUMENTS

| | | | | |
|---|---|---|---|---|
| CN | 102288830 | | 12/2011 | |
| CN | 102866300 | | 1/2013 | |
| CN | 204789762 | | 11/2015 | |
| CN | 106019160 | | 10/2016 | |
| CN | 206740861 | | 12/2017 | |
| DE | 102014008979 A1 | * | 11/2014 | ............. G01R 27/14 |
| EP | 1115171 A1 | | 7/2001 | |
| EP | 2338545 A1 | | 6/2011 | |
| EP | 2338546 A1 | | 6/2011 | |
| EP | 1619512 A2 | | 1/2012 | |
| WO | 2004/055536 A1 | | 7/2004 | |
| WO | 2012/022539 A1 | | 2/2012 | |
| WO | 2015/031334 A1 | | 3/2015 | |
| WO | 2017/006319 A1 | | 1/2017 | |
| WO | 2017/024411 A1 | | 2/2017 | |
| WO | 2019/115687 A1 | | 6/2019 | |

OTHER PUBLICATIONS

International Search Report dated Oct. 7, 2019, in Application No. PCT/EP2019/060276, 3 pp.

* cited by examiner

METHOD FOR DETERMINING THE SYSTEM RESISTANCE OF A HANDHELD MEDICAL DEVICE

CROSS-REFERENCE TO RELATED APPLICATIONS

This application is a continuation of International Patent Application No. PCT/EP2019/060276, filed 23 Apr. 2019, which claims the benefit of European Patent Application No. 18168884.7, filed 24 Apr. 2018, the disclosures of which are hereby incorporated herein by reference in their entirety.

TECHNICAL FIELD

The present disclosure relates to a method for determining a system resistance of a power supply of a handheld medical device and a respective handheld medical device. The method and device according to the present disclosure may be used in devices for detecting at least one analyte present in one or both of a body tissue or a body fluid, in particular the method and devices are applied in the field of detecting one or more analytes such as glucose, lactate, triglycerides, cholesterol or other analytes, typically metabolites, in body fluids such as blood, typically whole blood, plasma, serum, urine, saliva, interstitial fluid or other body fluids, both in the field of professional diagnostics and in the field of home monitoring. However, other fields of application are feasible.

BACKGROUND

Various types of power sources such as single-use or rechargeable batteries with different qualities are known and are used in handheld medical devices. A customer may be responsible for replacement of the power source in the handheld medical device. Battery life is a very difficult measurement to quantify. Changes in power source and aging of electrical contacts to the power source are also very difficult to characterize.

Use of electric double layer capacitors (EDLCs) in meters or insulin pumps as a design to detect and/or to temporarily bridge battery power failure and their use in first failure modes may be problematic due to the fact that these components are susceptible to quality problems and are also sensitive to changes in temperature and humidity. EDLCs may not be reliable and susceptible to losing their internal electrolyte which can cause short circuits on electronic boards as well as higher internal resistance, heating and shorter battery life.

WO 2017/006319 A1 describes method and system for monitoring the safety of a rechargeable Li-ion battery (LIB). An initial electrical state of the LIB is determined and altered by application or removal of DC electrical stimulus to trigger a time-varying response. The time-varying response of the LIB is measured, and at least one primary response parameter associated with the functional form of the measured response is extracted. At least one secondary response parameter is derived from the primary response parameter. A composite response parameter may be further derived from the primary response parameter and secondary response parameter. A likelihood of a short circuit precursor condition is determined in accordance with the primary response parameter, secondary response parameter and/or composite response parameter. Based on the determined likelihood, an alert of a potential short circuit derived hazard may be provided and/or a corrective measure to mitigate or prevent a short circuit derived hazard may be implemented. Quality control of power supply of a handheld medical device is not disclosed in WO 2017/006319 A1 but instead WO 2017/006319 A1 refers to safety monitoring for lithium-ion batteries in order to avoid safety hazards in laptops, cellphones, electric/hybrid vehicles and aircraft, see page 4, second paragraph of WO 2017/006319 A1. WO 2017/006319 A1 describes a specific approach of determining a system resistance, namely by determining a discharge curve, see FIGS. 5B and 5C and the corresponding description on pages 46 and 47. However, using a discharge curve is time consuming and slow since one has to wait for the discharge.

Despite the advantages and progress achieved by the above-mentioned developments, some significant technical challenges remain. In particular, known methods require determining a discharge curve used and thus, may be slow. Furthermore, in particular artificial or known loads are required, which require unnecessary loading of a battery which also consumes some part of the battery life.

BRIEF SUMMARY

It is against the above background that the embodiments of the present disclosure provide certain unobvious advantages and advancements over the prior art. In particular, the inventors have recognized a need for improvements in methods for determining the system resistance of a handheld medical device.

Although the embodiments of the present disclosure are not limited to specific advantages or functionality, it is noted that the present disclosure provides a method for determining a system resistance and a handheld medical device, which at least partially avoid the shortcomings of known devices and methods of this kind and which at least partially address the above-mentioned challenges. Specifically, effective and fast quality control of at least one power supply shall be possible.

In accordance with one embodiment of the present disclosure, a method for determining system resistance of at least one power supply of a handheld medical device if provided, the method comprising: a) generating at least one excitation voltage signal, wherein the excitation voltage signal comprises at least one direct current (DC) voltage signal, wherein the excitation voltage signal has a fast transition DC flank of 20 ns or less; b) applying the excitation voltage signal to at least one reference resistor having a predetermined or pre-defined resistance value, wherein the reference resistor is arranged in series with the power supply; c) measuring a response signal of the power supply; d) determining a signal flank from the response signal and determining an ohmic signal portion from one or both of shape and height of the signal flank; and e) determining the system resistance of the power supply from the ohmic signal portion.

In accordance with another embodiment of the present disclosure, a handheld medical device is provided comprising: at least one power supply for powering to at least one element of the handheld medical device; at least one reference resistor having a predetermined or predefined reference resistance, wherein the reference resistor is arranged in series with the power supply; at least one signal generator device adapted to generate at least one excitation voltage signal, wherein the excitation voltage signal comprises at least one direct current (DC) voltage signal, wherein the DC voltage signal has a fast transition DC flank from 20 ns or less, wherein the signal generator device is adapted to apply the excitation voltage signal to the reference resistor; at least one measurement unit adapted to receive at least one response signal; at least one evaluation device adapted to determine a signal flank from the response signal and to determine an ohmic signal portion from one or both of shape and height of the signal flank, wherein the evaluation device is adapted to determine a system resistance of the power supply from the ohmic signal portion.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRITION OF THE DRAWINGS

The following detailed description of the embodiments of the present disclosure can be best understood when read in conjunction with the following drawings, where like structure is indicated with like reference numerals and in which.

Figure 1:
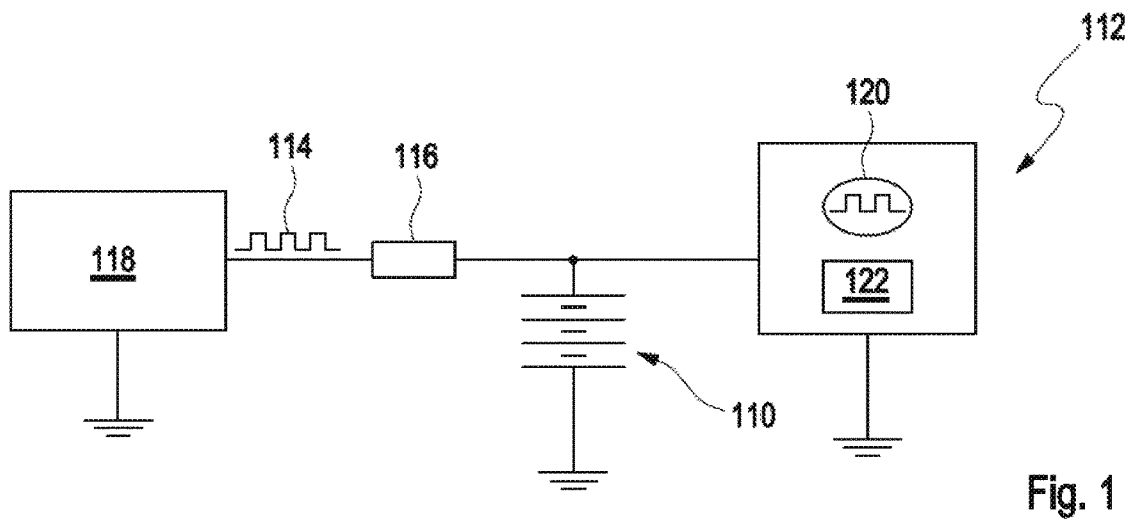
FIG. 1 shows a test setup for performing a method for determining system resistance of a power supply of a handheld medical device according to the present disclosure.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

As used in the following, the terms "have", "comprise" or "include", or any arbitrary grammatical variations thereof, are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may refer both to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once, typically will be used only once, when introducing the respective feature or element. In the following, in most cases, when referring to the respective feature or element, the expressions "at least one" or "one or more" will not be repeated, notwithstanding the fact that the respective feature or element may be present once or more than once.

Further, as used in the following, the terms "preferably", "more preferably", "typically", "more typically", "particularly", "more particularly", "specifically", "more specifically" or similar terms are used in conjunction with optional features, without restricting alternative possibilities. Thus, features introduced by these terms are optional features and are not intended to restrict the scope of the claims in any way. The disclosure may, as the skilled person will recognize, be performed by using alternative features. Similarly, features introduced by "in an embodiment of the disclosure" or similar expressions are intended to be optional features without any restriction regarding alternative embodiments of the disclosure, without any restrictions regarding the scope of the disclosure and without any restriction regarding the possibility of combining the features introduced in such a way with other optional or non-optional features of the disclosure.

In a first aspect of the present disclosure, a method for determining system resistance of at least one power supply of a handheld medical device is disclosed. As used herein, the term "handheld medical device" refers to an arbitrary portable medical device. The handheld medical device may be selected from the group consisting of: at least one handheld analytical device, in particular at least one handheld meter such as a blood glucose meter; at least one insulin pump; at least one portable sensor for monitoring at least one body function such as at least one long-term ECG, an implantable or insertable continuous glucose sensor. The handheld medical device may be any device which requires the use of a low voltage high capacitive power source in which loss of this source could lead to loss of system functionality or loss of data as in the case of supplying data storage devices which require a constant power source. The lower the voltage of the power supply source the more of an impact system resistance can have. Generally, there are a limitless number of devices which use low voltage sources to power their systems or any system which requires a critical power supply which needs a first failure mode to monitor the supply, such as on the field of portable medical devices or in portable medical applications.

As used herein, the term "power supply" refers to at least one unit or system of the handheld medical device adapted to provide power to at least one element of the handheld medical device such as to at least one functional unit of the handheld medical device, e.g., at least one sensor element, and/or at least one control unit, and/or at least one actuation unit of the handheld medical device. The power supply may comprise at least one element selected from the group consisting of: at least one power source; at least one electrical contact; at least one supply line. The power source may comprise at least one power source selected from the group consisting of: at least one battery, e.g., at least one coin battery, at least one AA, AAA or other battery; at least one rechargeable battery; at least one electric double layer capacitor (EDLC).

As used herein the term "system resistance" refers to a resistance value of the power supply, in particular internal resistance of the power supply. The system resistance may comprise resistance of the at least one electrical contact of the power supply and/or line resistances and/or internal resistances in the power source, for example, due to aging or temperature. The system resistance may comprise resistance due to creepage current. For example, creepage current may result from unwanted current paths between two electrodes such that system voltage will drop. The system resistance may comprise resistance due to corrosion between contacts and/or reduction of capacity through chemical changes in the EDLC or battery. As further used herein, the term "system" refers to an arbitrary set of interacting or interdependent component parts forming a whole. Specifically, the components may interact with each other in order to fulfill at least one common function. At least two components may be handled independently or may be coupled or connectable. As used herein, the term "determining system resistance" refers to detecting and/or monitoring the system resistance.

The method steps may be performed in the given order. However, other orders of the method steps are feasible. Further, one or more of the method steps may be performed in parallel and/or in a time overlapping fashion. Further, one or more of the method steps may be performed repeatedly. Further, additional method steps may be present which are not listed.

In accordance with one embodiment, the method comprises the following steps:
  a) generating at least one excitation voltage signal, wherein the excitation voltage signal comprises at least one direct current (DC) voltage signal, wherein the DC voltage signal has a fast transition DC flank from 20 ns or less;
  b) applying the excitation voltage signal to at least one reference resistor having a predetermined or pre-defined resistance value, wherein the reference resistor is arranged in series with the power supply;
  c) measuring a response signal of the power supply;
  d) determining a signal flank from the response signal and determining an ohmic signal portion from one or both of shape and height of the signal flank;
  e) determining the system resistance of the power supply from the ohmic signal portion.

As used herein, the term "at least one excitation voltage signal" generally refers to at least one arbitrary voltage signal. The excitation voltage signal comprises at least one direct current (DC) voltage signal. The excitation voltage signal may comprise a square wave signal and/or a sine wave signal. For example, the excitation voltage signal may be a sine wave signal, wherein a frequency of the excitation voltage signal may be from 20 Hz to 300 kHz. Generally, it is possible to pulse down to seconds, minutes, hours or even days.

Only one fast transition pulse is needed to gather the system resistance data. The frequency may depend on the system under test and how quickly the system resistance information is required in order to make a decision. For example, system resistance information may be needed every 50 milliseconds. The excitation voltage signal may comprise a non-continuous signal such as a pulse. Specifically, the excitation voltage signal may comprise a fast transition square wave. The excitation voltage signal may be applied during at least one test sequence, for example, a time sequence. With respect to further embodiments of the excitation voltage signal reference is made to International Publication No. WO 2019/115687 A1, the full content of which is herewith included by reference.

The excitation voltage signal has fast transition DC flank of 20 ns or less, typically of 10 ns or less, most typically of 5 ns or less. For example, the excitation voltage signal may comprise a repeatable cycle, wherein the repeatable cycle comprises at least one excitation signal flank. As used herein, the term "transition flank" or "signal flank" refers to transition of the excitation from low to high signal value or from high to low signal value. The excitation signal flank may be a rising signal flank or a falling signal flank. The signal flank of the excitation voltage signal may have a change in signal from a first point of the signal flank to a second point of the excitation signal flank in a microsecond to nanosecond range. As used herein, the term "fast transition DC flank" refers to a transition DC flank which speeds on the order of 20 ns or less, in particular of between 5 to 20 ns. The terms first and second "point" refer to regions or points of the signal. The first point may be a local and/or overall minimum of the excitation voltage signal. The first point may be a first plateau of the excitation voltage signal. The first point may be a through or low value of the signal. The second point may be a local and/or overall maximum of the excitation signal. The second point may be a second plateau of the excitation voltage signal, which may be reached during application of the excitation voltage signal. The second point may be a peak or high value of the signal. The excitation voltage signal may be or may comprise a fast transition square wave. The fast transition square wave may have the rising signal flank as described above. Specifically, the fast transition square wave may have a change in signal from the first point of the excitation signal flank to the second point of the excitation signal flank below or equal 50 ns, typically below or equal 20 ns. Using an excitation voltage signal having a fast transition DC flank allows separating ohmic signal portion and imaginary signal portion of the power supply, as will be outlined below, and thus, may allow a simplified analysis of the response signal and determination of the system resistance from the ohmic signal portion.

The excitation voltage signal may be generated by at least one signal generator device. The term "signal generator device" generally refers to a device, for example, a voltage source, being configured to generate a voltage signal. The signal generator device may comprise at least one voltage source. The signal generator device may comprise at least one function generator selected from the group consisting of: at least one square wave generator and at least one sine wave generator. The signal generator device may comprise at least one fast transition square ware oscillator comprising one or more Schmitt triggers, a fast I/O pin configured as an output, Flip/Flop, Transistor configured as a switch, a DAC (Digital to Analog Converter), an arbitrary wave generator configured as a single shot or square wave generator. The signal generator device may be part of measurement electronics and/or may be connected to the measurement electronics of the handheld medical device. The signal generator device may be part of the measurement electronics, such as of an evaluation device, or may be designed as a separate device.

The excitation voltage signal is applied to the at least one reference resistor having a predetermined or pre-defined resistance value. As used herein, the term "reference resistor" refers to a resistor having a predetermined or pre-defined resistance value. The reference resistance may be an average value determined, specifically predetermined, from a plurality of reference measurements. The reference resistance may be selected suitable for determining a value to be measured such as the ohmic signal portion. The reference resistance may be suitably determined for an expected measurement range of the system to be measured. For example, when a battery to be implemented has a working range in milliohm or tens of ohms range, the reference resistor may be selected to have a value in the middle of the measurement range of interest. With metabolic sensors as an example this may be in k$\Omega$, so the reference resistor may be selected to be a k$\Omega$ reference resistor. The reference resistor may be connected, e.g., directly or by an electrical line, to at least one electrical contact of the power supply. The power supply may comprise two electrical contacts, wherein a first electrical contact may be connected at least to the reference resistor and a second electrical contact may be connected to ground. The signal generator device may be adapted to apply the excitation voltage signal to the reference resistor. The reference resistor may be connected to at least one output terminal of the signal generator device. The reference resistor is arranged in series with the power supply. For example, the reference resistor may comprise a first electrical contact which may be connected, e.g., directly or indirectly using electrical line, to the output terminal of the signal generator device. The reference resistor may comprise a second electrical contact which may be connected, e.g., directly or indirectly using electrical line, to at least one electrical contact of the power supply.

Known methods for determining system resistance use a resulting discharge curve from opening the cell, as described, e.g., in documents WO 2017/006319 A1. In contrast thereto, in the method according to the present disclosure the response signal to the application of the very short pulse signal may be used and the ohmic signal portion may be derived therefrom. This may allow fast determining of the system resistance, specifically faster compared to methods using and thus, waiting for the resulting discharge curve. Moreover, as mentioned above, this may allow avoiding unnecessary loading of the battery using a load to measure the discharge. This may be especially advantageous with batteries which have small capacities.

In step c), the response signal of the power supply is measured. As outlined above, the reference resistor and the power supply are arranged in series. If the excitation voltage signal is applied to the reference resistor current flows through the resistor to the power supply. As used herein, the term "response signal" generally refers to a voltage change at the reference resistor in response to the applied excitation voltage signal which, for example, may be determined between the reference resistor and the power supply. The response signal may be measured by using at least one measurement unit. The measurement unit may comprise at least one response signal detector, for example at least one signal analyzer and/or at least one oscilloscope. The response signal may be a current response signal, wherein a measured response voltage can be determined using a current to voltage converter.

In step d), a signal flank from the response signal is determined and an ohmic signal portion is determined from one or both of shape and height of the signal flank. As outlined above, using DC voltage signals having a fast transition flank allows for separation of ohmic signal portion and imaginary signal portion. As used herein, "ohmic signal portion" refers to real part of the impedance Z. The response signal may comprise the ohmic signal portion in complex impedance. The complex impedance Z may be described as Z=R+iX, wherein R is the real part of the complex impedance and X is the imaginary part of the complex impedance.

In polar form the complex impedance may be described as $Z=|Z|e^{i\theta}$, wherein $\theta$ is the phase difference between voltage and current. The admittance Y may be defined as $$Y = \frac{1}{Z}.$$

Thus, the complex impedance information refers to one or more of information about admittance, in particular an admittance value, phase information, information about real part and/or imaginary part. The response signal may comprise an ohmic signal portion and a non-ohmic signal portion due to capacitive parts of the power supply. By analyzing one or both of signal shape and signal height of the response signal, the ohmic signal portion can be determined. The ohmic signal portion may be determined by comparing shape and/or height of the excitation voltage signal and the shape and/or height of the response signal. The response signal may comprise at least one signal flank, in particular at least one rising signal flank. Through characterization of the induced square wave or sine voltage signal, the ohmic signal portion can be determined from the signal flank of the response signal. In particular, by analyzing one or both of signal shape and signal height of the response signal separation of the real and imaginary part of the response signal may be possible. Step d) may comprise determining at least one deviation and/or difference from an induced signal shape and/or height of the excitation voltage signal. In particular, deviations and/or differences from the induced signal shape and/or height may be determined. It was found that the response signal exhibits, in comparison to the excitation voltage signal, a vertical drop due to voltage drop at the power supply and subsequent rising signal flank due to charging integration from the capacitive parts of the power supply, denoted as rising signal flank in the following. The term "voltage drop" generally refers to change, for example lowering, in voltage. The voltage drop may result from presence of system resistance. The voltage drop may be an observable voltage change. For example, the voltage may show deviations from a high value from 5 to 50%. System resistance detection could also detect quick resistance change transients which could impact system performance. The ohmic signal portion of the response signal may be identified by determining a voltage drop value, i.e., a voltage value at start of the rising signal flank. In step e) the system resistance of the power supply is determined from the ohmic signal portion. Specifically, the system resistance $R_{system}$, of the power supply may be determined by $$R_{system} = \frac{U_{measured} * R_{ref}}{U_{target} - U_{measured}},$$

wherein $U_{target}$ is a pulse height of the excitation voltage signal, $R_{ref}$ is the reference resistance and $U_{measured}$ is a height of the response signal at the start of the rising signal flank, i.e., the ohmic signal portion. The pulse height of the excitation voltage signal $U_{target}$ may be pre-known or pre-determined value. The induced signal shape and/or height may be determined, e.g., pre-determined and/or determined during the method. For example, the method may comprise determining a pulse shape and/or height of the excitation voltage signal. For example, the output terminal of the signal generator device may be connected to the at least one measurement unit which may be adapted to receive the excitation voltage signal and to determine the pulse height of the excitation voltage signal. The excitation voltage signal $U_{target}$ may be determined such as by using at least one analog-digital-converter which may be placed in series and between the signal generator device and the reference resistor. Additionally, or alternatively, the excitation voltage signal may be known by design, and therefore presumed to be a certain value. In this case, an analog-to-digital-converter may not be needed, saving costs in design.

The method may comprise at least one condition determining step, wherein at least one condition information of the power supply may be determined by comparing the determined system resistance of the power supply with at least one predetermined or predefined system resistance value. The condition information may be at least one information selected from the group consisting of: at least one information about the power supply life, e.g., the battery life, at least one information about charging, at least one information about changes; at least one information about suitability and/or aging of electrical contacts. Additionally or alternatively, moisture as part of the system resistance can be detected and/or determined. This may be important if the layout on a printed circuit board does not allow enough separation between the + and − potential points leading to current creepage. Detection of moisture could also be used as a first failure detection, if the medical device is subjected to high moisture environments or extreme changes in temperature over a short period of time. System resistance detection could also detect quick resistance change transients which could impact system performance. Furthermore, transients from electrostatic discharge (ESD) events could possibly be detected. Furthermore, contact pressure due to aging may also have an impact on the system resistance. Furthermore, the method may be used for testing and/or monitoring activation processes of zinc-air batteries, which require oxygen for their activation. In particular, the method may allow determining how well the battery has reacted to the incoming air and if the battery has reached a certain value to properly supply the system with power. The method may comprise monitoring the condition information over time. The predetermined resistance value may be a system resistance value determined in a previous measurement. The predetermined resistance value may be an average system resistance value determined by determining an average value of at least two previous measurements of the system resistance. The condition information may be determined repeatedly, for example continuously or non-continuously, e.g., in a pre-defined interval, such as every 50 ms. However, other embodiments and time intervals are possible. The condition determining step may be performed in a manufacturing stage and/or by an electronic manufacturing service to characterize the power supply, in particular used batteries or EDLCs. The condition determining step may be performed for determining requirement definitions, e.g., for suppliers of batteries or EDLCs.

The method may comprise at least one failsafe step. As used herein, the term "failsafe step" refers to at least one step ensuring to prevent power failure and/or malfunctions caused by damaged and/or aberrant power supplies in handheld medical devices. In the failsafe step the determined system resistance of the power supply may be compared to at least one predetermined or predefined threshold value. Based on the comparison at least one failsafe decision may be determined and/or at least one failsafe action may be performed. For example, the failsafe step may comprise issuing and/or displaying a notification such as an error message in case the system resistance exceeds the threshold value and/or exceeds the threshold value by a predefined or predetermined value. The failsafe step may comprise displaying a warning, such as a visual and/or acoustic indication, in case the system resistance exceeds the threshold value and/or exceeds the threshold value by a predefined or predetermined value. In the failsafe step a warning may be generated if the determined system resistance exceeds the threshold value by a predefined or predetermined value, for example by 10%. In the failsafe step an abortion of the power supply may be initiated if the determined system resistance exceeds the threshold value by a predefined or predetermined value, for example by 10%. The threshold value may be determined or determinable empirically, analytically or else semi-empirically. The threshold value may be provided in at least one look-up table and/or may be deposited and/or stored, for example, in a storage of the handheld medical device. The threshold value may be determined at begin of operation of the power supply and/or shortly after at begin of use of the power supply, such as after replacement of the battery. For example, the threshold value may be at least one upper limit of a system resistance. For example, the resistance limit may be 500 m$\Omega$, typically 100 m$\Omega$, most typically 20 m$\Omega$. Optimal inner resistances may be in the region of milliohm. For example, system resistances could generate several ohms when considering just the power source. The failsafe step may comprise comparing the determined system resistance with a plurality of resistance values. The failsafe step may comprise storing, e.g., within a measurement engine electronic, for example, of the evaluation device, pre-determined and/or pre-defined resistance limits. The failsafe step may be performed before and/or during operation of the element powered by the power supply. The failsafe step may be performed repeatedly, for example in a pre-defined interval, such as every 50 ms. However, other embodiments and time intervals are possible. For example, intervals such as seconds, minutes, days even weeks may be possible.

The disclosure further provides and proposes a computer program including computer-executable instructions for performing the method according to the present disclosure in one or more of the embodiments enclosed herein, when the program is executed on a computer or computer network. Specifically, the computer program may be stored on a computer-readable data carrier. Thus, specifically, one, more than one or even all of method steps, as indicated above, may be performed by using a computer or a computer network, typically by using a computer program.

The disclosure further provides and proposes a computer program product having program code means, in order to perform the method for determining system resistance of a power supply of a handheld medical device according to the present disclosure in one or more of the embodiments enclosed herein, when the program is executed on a computer or computer network. Specifically, the program code means may be stored on a computer-readable data carrier.

Further, the disclosure provides and proposes a data carrier having a data structure stored thereon, which, after loading into a computer or computer network, such as into a working memory or main memory of the computer or computer network, may execute the method according to one or more of the embodiments disclosed herein.

The disclosure further provides and proposes a computer program product with program code means stored on a machine-readable carrier, in order to perform the method according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, the disclosure provides and proposes a modulated data signal which contains instructions readable by a computer system or computer network, for performing the method according to one or more of the embodiments disclosed herein.

Typically, referring to the computer-implemented aspects of the disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, the present disclosure further provides:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer program, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, and a computer program product having program code means, wherein the program code means can be stored or are stored on a storage medium, for performing the method according to one of the embodiments described in this description, if the program code means are executed on a computer or on a computer network.

In a further aspect of the present disclosure, a handheld medical device is provided. The handheld medical device comprises at least one power supply for powering to at least one element of the handheld medical device;

at least one reference resistor having a predetermined or pre-defined reference resistance, wherein the reference resistor is arranged in series with the power supply;

at least one signal generator device adapted to generate at least one excitation voltage signal, wherein the excitation voltage signal comprises at least one direct current (DC) voltage signal, wherein the DC voltage signal has a fast transition DC flank from 20 ns or less, wherein the signal generator device is adapted to apply the excitation voltage signal to the reference resistor;

at least one measurement unit adapted to receive at least one response signal;

at least one evaluation device adapted to determine a signal flank from the response signal and to determine an ohmic signal portion from one or both of shape and height of the signal flank, wherein the evaluation device is adapted to determine a system resistance of the power supply from the ohmic signal portion.

The handheld medical device may be adapted to perform the method for determining system resistance according to one or more of the embodiments of the method according to the present disclosure. For definitions of the features of the handheld medical device and for optional details of the handheld medical device, reference may be made to one or more of the embodiments of the method as disclosed above or as disclosed in further detail below.

The term "measurement unit" generally may refer to an arbitrary device, typically an electronic device, which may be configured to detect at least one signal, in particular the response signal. The measurement unit may be adapted to detect the response signal generated in response to the excitation voltage signal. The measurement unit and the evaluation device may be designed as at least partially separated components. The measurement unit may be part of the evaluation device or may be designed as separate device. As used herein, the term "evaluation device" generally refers to an arbitrary device being configured to determine the signal flank from the response signal, to determine the ohmic signal portion from one or both of shape and height of the signal flank and to determine a system resistance of the power supply from the ohmic signal portion. The evaluation device may be configured to evaluate the response. The evaluation device may comprise at least one microprocessor. As an example, the evaluation device may be or may comprise one or more integrated circuits, such as one or more application-specific integrated circuits (ASICs), and/or one or more data processing devices, such as one or more computers, typically one or more microcomputers and/or microcontrollers. Additional components may be comprised, such as one or more preprocessing devices and/or data acquisition devices, such as one or more devices for receiving and/or preprocessing of the electrode signals, such as one or more converters and/or one or more filters. Further, the evaluation device may comprise one or more data storage devices. Further, as outlined above, the evaluation device may comprise one or more interfaces, such as one or more wireless interfaces and/or one or more wire-bound interfaces. The evaluation device may comprise at least one analog-to-digital convertor (ADC) and/or at least one digital-to-analog convertor (DAC). For example, the ADC may be a 10 to 12 bit ADC, for example of the microprocessor. The evaluation device may comprise one or more of at least one microprocessor; a cellular phone; a smart phone; a personal digital assistant.

The handheld medical device may comprise at least one control unit and/or at least one actuation unit and/or may be adapted to be controlled by at least one control unit and/or by at least one actuation unit. As used herein, the term "control unit" refers to at least one unit adapted to control the handheld medical device such as to control operation of the handheld device, e.g., operation of an insulin pump, and/or to control at least one function of the handheld device. As used herein, the term "actuation unit" refers to at least one unit adapted to actuate at least one function of the handheld medical device. The control unit and/or the actuation unit may comprise at least one microprocessor. As an example, the control unit and/or the actuation unit may be or may comprise one or more integrated circuits, such as one or more application-specific integrated circuits (ASICs), and/or one or more data processing devices, such as one or more computers, typically one or more microcomputers and/or microcontrollers. Further, the control unit and/or the actuation unit may comprise one or more interfaces, such as one or more wireless interfaces and/or one or more wirebound interfaces. The control unit and/or the actuation unit may be or may comprise one or more of a cellular phone; a smart phone; a personal digital assistant.

The handheld medical device may comprise at least one power supply circuit configured for providing power to the at least one element of the handheld medical device and at least one system resistance measurement circuit configured for determining the system resistance. As used herein, the term "system resistance measurement circuit" refers to an electrical circuit comprising at least one electronic component. For example, the system resistance measurement circuit may comprise the power supply and the reference resistor connected to the signal generator device and to measurement unit, as described above. The handheld medical device may comprise at least one switching element adapted to separate the power supply circuit and the system resistance measurement circuit and/or to switch between the power supply circuit and the system resistance measurement circuit. The switching element may be a switching element selected from the group consisting of: at least one analog switch, at least one diode, at least one field effect transistor (FET). The handheld medical device may be adapted to operate in at least two operational modes. In a first operational mode the handheld medical device may be adapted to determine the system resistance and in a second operational mode the power supply of the handheld medical device may be adapted to provide power to the at least one element of the handheld medical device.

The proposed method and the handheld medical device provide many advantages over known devices and methods. The proposed method and handheld medical device allow effective and fast quality control of the power supply of the handheld medical device. Specifically, the proposed method and the handheld medical device may allow reliably determining undervoltage or battery failure of the power supply of the handheld medical device. Furthermore specifically, the proposed method and handheld medical device allow rapid and reliable on-board measurement of system resistance of a power supply with high simplicity and at low costs. In particular, using an excitation voltage signal having a fast transition DC flank allows separating ohmic signal portion and imaginary signal portion of the power supply and thus, simplified analysis of the response signal and determination of the system resistance from the ohmic signal portion. Thus, rapid determining of system resistance and rapid determining of information about the power supply, e.g., battery life and/or information about charging, and/or changes, in particular defects, and/or information about aging of electrical contacts may be possible. Moreover, simple implementation into standard or available hardware of handheld medical devices is possible, for example by using a standard 10 bit to 12 bit ADC which is found in common microprocessors today. Furthermore, the simplified analysis using the ohmic signal portion allows the measured response data to remain in the time domain such that there is no need for transformation into the frequency domain, which would require hardware complexity. Thus, it is possible to use parts of standard or available hardware of handheld medical devices such as a standard microprocessor. Moreover specifically, such a design of a handheld medical device would be relatively simple and cost effective lowering the risk of bad parts, raising the power performance and making the handheld medical device safer and more robust. An advantage to the use of the DC pulse is that it is not required to transform from a time based measurement to a frequency based measurement, e.g., by Fourier transformation, which requires code space and hardware complexities. A further advantage is that it may be possible to reduce measurement duration, specifically to reduce measurement times, measurement periods, acquisition times or test times. In particular, it may be possible to monitor quality of the power supply in subsequent very short time intervals and to allow for quasi-continuous monitoring.

Summarizing the findings of the present disclosure, the following embodiments are typical:

Embodiment 1: Method for determining system resistance of at least one power supply of a handheld medical device, the method comprising
 a) generating at least one excitation voltage signal, wherein the excitation voltage signal comprises at least one direct current (DC) voltage signal, wherein the excitation voltage signal has a fast transition DC flank of 20 ns or less;
 b) applying the excitation voltage signal to at least one reference resistor having a predetermined or pre-defined resistance value, wherein the reference resistor is arranged in series with the power supply,
 c) measuring a response signal of the power supply;
 d) determining a signal flank from the response signal and determining an ohmic signal portion from one or both of shape and height of the signal flank;
 e) determining the system resistance of the power supply from the ohmic signal portion.

Embodiment 2: The method according to the preceding embodiment, wherein the excitation voltage signal comprises a square wave signal or a sine wave signal.

Embodiment 3: The method according to any one of the preceding embodiments, wherein the excitation voltage signal comprises a non-continuous signal such as a pulse.

Embodiment 4: The method according to any one of the preceding embodiments, wherein the reference resistor is connected to at least one electrical contact of the power supply.

Embodiment 5: The method according to any one of the preceding embodiments, wherein step d) comprises determining at least one deviation and/or difference from an induced signal shape of the excitation voltage signal.

Embodiment 6: The method according to any one of the preceding embodiments, wherein the system resistance $R_{system}$ of the power supply is determined by $$R_{system} = \frac{U_{measured} * R_{ref}}{U_{target} - U_{measured}},$$

wherein $U_{target}$ is a pulse height of the excitation voltage signal, $R_{ref}$ is the reference resistance and $U_{measured}$ is a height of the response signal at a start of a rising signal flank of the response signal.

Embodiment 7: The method according to any one of the preceding embodiments, wherein the method comprises at least one condition determining step, wherein at least one condition information of the power supply is determined by comparing the determined system resistance of the power supply with at least one predetermined or predefined system resistance value.

Embodiment 8: The method according to any one of the preceding embodiments, wherein the method comprises at least one failsafe step, wherein in the failsafe step the determined system resistance of the power supply is compared to at least one predetermined or predefined threshold value.

Embodiment 9: The method according to the preceding embodiment, wherein in the failsafe step a warning is generated if the determined system resistance exceeds the threshold value by a predefined or predetermined value.

Embodiment 10: The method according to any one of the two preceding embodiments, wherein in the failsafe step an abortion of the power supply is initiated if the determined system resistance exceeds the threshold value by a predefined or predetermined value.

Embodiment 11: A computer program including computer-executable instructions for performing the method for determining the system resistance according to any of the preceding embodiments when the program is executed on a computer or computer network.

Embodiment 12: A computer-readable medium having computer-executable instructions for performing the method for determining the system resistance according to any of the preceding embodiments, wherein the computing device is provided by a computer.

Embodiment 13: A computer program product with program code means stored on a machine-readable carrier, in order to perform the method for determining the system resistance according to any of the preceding embodiments, when the program is executed on a computer or computer network.

Embodiment 14: Handheld medical device comprising
at least one power supply for powering to at least one element of the handheld medical device;
at least one reference resistor having a predetermined or pre-defined reference resistance, wherein the reference resistor is arranged in series with the power supply;
at least one signal generator device adapted to generate at least one excitation voltage signal, wherein the excitation voltage signal comprises at least one direct current (DC) voltage signal, wherein the DC voltage signal has a fast transition DC flank from 20 ns or less, wherein the signal generator device is adapted to apply the excitation voltage signal to the reference resistor;
at least one measurement unit adapted to receive at least one response signal;
at least one evaluation device adapted to determine a signal flank from the response signal and to determine an ohmic signal portion from one or both of shape and height of the signal flank, wherein the evaluation device is adapted to determine a system resistance of the power supply from the ohmic signal portion.

Embodiment 15: The handheld medical device according to the preceding embodiment, wherein the handheld medical device is selected from the group consisting of: at least one handheld analytical device such as at least one handheld meter; at least one insulin pump; at least one portable sensor for monitoring at least one body function such as at least one long-term ECG, an implantable or insertable continuous glucose sensor.

Embodiment 16: The handheld medical device according to any one the preceding embodiments referring to a handheld medical device, wherein the power supply comprises at least one power source selected from the group consisting of: at least one battery; at least one rechargeable battery, at least one electric double layer capacitor (EDLC).

Embodiment 17: The handheld medical device according to any one the preceding embodiments referring to a handheld medical device, wherein the evaluation device comprises one or more of at least one microprocessor; a cellular phone; a smart phone; a personal digital assistant.

Embodiment 18: The handheld medical device according to any one the preceding embodiments referring to a handheld medical device, wherein the evaluation device comprises at least one analog-to-digital convertor (ADC) and/or at least one digital-to-analog convertor (DAC).

Embodiment 19: The handheld medical device according to any one the preceding embodiments referring to a handheld medical device, wherein the handheld medical device comprises at least one power supply circuit configured for providing power to the at least one element of the handheld medical device and at least one system resistance measurement circuit configured for determining the system resistance, wherein the handheld medical device comprises at least one switching element adapted to separate the power supply circuit and the system resistance measurement circuit.

In order that the embodiments of the present disclosure may be more readily understood, reference is made to the following examples, which are intended to illustrate the disclosure, but not limit the scope thereof.

FIG. 1 shows a test setup for performing a method for determining system resistance of a power supply 110 of a handheld medical device 112 according to the present disclosure. The power supply 110 may comprise at least one element selected from the group consisting of at least one power source; at least one electrical contact; at least one supply line. The power source 110 may comprise at least one power source selected from the group consisting of: at least one battery, e.g., at least one coin battery, at least one AA, AAA or other battery; at least one rechargeable battery; at least one electric double layer capacitor (EDLC). In the embodiment shown in FIG. 1, the power supply may comprise a battery.

The method comprises the following steps:
a) generating at least one excitation voltage signal (denoted in FIG. 1 with reference number 114), wherein the excitation voltage signal comprises at least one direct current (DC) voltage signal, wherein the DC voltage signal has a fast transition DC flank from 20 ns or less;
b) applying the excitation voltage signal 114 to at least one reference resistor 116 having a predetermined or pre-defined resistance value, wherein the reference resistor 116 is arranged in series with the power supply 110,
c) measuring a response signal of the power supply;
d) determining a signal flank from the response signal and determining an ohmic signal portion from one or both of shape and height of the signal flank;
e) determining the system resistance of the power supply 116 from the ohmic signal portion.

The excitation voltage signal 114 comprises at least one direct current (DC) voltage signal. The excitation voltage signal 114 may comprise a square wave signal and/or a sine wave signal. For example, the excitation voltage signal 114 may be a sine wave signal, wherein a frequency of the excitation voltage signal 114 may be from 20 Hz to 300 kHz. The excitation voltage signal 114 may comprise a non-continuous signal such as a pulse. The excitation voltage signal 114 has fast transition DC flank of 20 ns or less, typically of 10 ns or less, most typically of 5 ns or less. For example, the excitation voltage signal 114 may comprise a repeatable cycle, wherein the repeatable cycle comprises at least one excitation signal flank. The excitation signal flank may be a rising signal flank or a falling signal flank. The signal flank of the excitation voltage signal 114 may have a change in signal from a first point of the signal flank to a second point of the excitation signal flank in a microsecond to nanosecond range. The first point may be a local and/or overall minimum of the excitation voltage signal 114. The first point may be a first plateau of the excitation voltage signal. The first point may be a through or low value of the signal. The second point may be a local and/or overall maximum of the excitation voltage signal. The second point may be a second plateau of the excitation voltage signal 114, which may be reached during application of the excitation voltage signal 114. The second point may be a peak or high value of the signal. The excitation voltage signal 114 may be generated by at least one signal generator device 118. The signal generator device 118 may comprise at least one voltage source. The signal generator device 118 may comprise at least one function generator selected from the group consisting of: at least one square wave generator and at least one sine wave generator. The signal generator device 118 may comprise at least one fast transition square ware oscillator comprising one or more Schmitt triggers. The signal generator device 118 may be part of measurement electronics and/or may be connected to the measurement electronics of the handheld medical device 112. The signal generator device 118 may be part of the measurement electronics, such as of an evaluation device, or may be designed as a separate device.

The excitation voltage signal 114 is applied to the at least one reference resistor 116 having a predetermined or pre-defined resistance value. The reference resistance may be an average value determined, specifically pre-determined, from a plurality of reference measurements. The reference resistor 116 may be connected, e.g., directly or by an electrical line, to at least one electrical contact of the power supply 110. The power supply 110 may comprise two electrical contacts, wherein a first electrical contact may be connected at least to the reference resistor 116 and a second electrical contact may be connected to ground. The reference resistor 116 may be connected to at least one output terminal of the signal generator device 118. The reference resistor 116 is arranged in series with the power supply 110. For example, the reference resistor 116 may comprise a first electrical contact which may be connected, e.g., directly or indirectly using electrical line, to the output terminal of the signal generator device 118. The reference resistor 116 may comprise a second electrical contact which may be connected, e.g., directly or indirectly using electrical line, to at least one electrical contact of the power supply 110. The signal generator 118 may be connected through the reference resistor 116 to the power supply 110. For example, the reference resistor 116 may have a resistance of 56Ω.

In step c), the response signal of the power supply 110 is measured. As outlined above, the reference resistor 116 and the power supply 110 are arranged in series. If the excitation voltage signal 114 is applied to the reference resistor current flows through and from the resistor 116 to the power supply 110. The response signal may be measured by using at least one at least one measurement unit 120. The measurement unit 120 may comprise at least one response signal detector, for example at least one signal analyzer and/or at least one oscilloscope. The response signal may be a current response signal, wherein a measured response voltage can be determined using a current to voltage converter. In FIG. 1, the measurement unit 120 may be an oscilloscope with a 10 MΩ input.

In step d), in particular by using at least one evaluation device 122, a signal flank from the response signal is determined and an ohmic signal portion is determined from one or both of shape and height of the signal flank. As outlined above, using DC voltage signals having a fast transition flank allows for separation of ohmic signal portion and imaginary signal portion. The response signal may comprise an ohmic signal portion and a non-ohmic signal portion due to capacitive parts of the power supply. By analyzing one or both of signal shape and signal height of the response signal, the ohmic signal portion can be determined. The ohmic signal portion may be determined by comparing shape and/or height of the excitation voltage signal 114 and the shape and/or height of the response signal. The response signal may comprise at least one signal flank, in particular at least one rising signal flank. Through characterization of the induced square wave or sine voltage signal, the ohmic signal portion can be determined from the signal flank of the response signal. In particular, by analyzing one or both of signal shape and signal height of the response signal separation of the real and imaginary part of the response signal may be possible. Step d) may comprise determining at least one deviation and/or difference from an induced signal shape and/or height of the excitation voltage signal. In particular, deviations and/or differences from the induced signal shape and/or height may be determined. It was found that the response signal exhibits, in comparison to the excitation voltage signal, a vertical drop due to voltage drop at the power supply and subsequent rising signal flank due to charging integration from the capacitive parts of the power supply, denoted as rising signal flank in the following. The voltage drop may result from presence of system resistance. The voltage drop may be an observable voltage change. For example, the voltage may show deviations from a high value from 5 to 50%. System resistance detection could also detect quick resistance change transients which could impact system performance. The ohmic signal portion of the response signal may be identified by determining a voltage drop value, i.e., a voltage value at start of the rising signal flank.

In step e) the system resistance of the power supply 110 is determined from the ohmic signal portion, in particular by using the evaluation device 122. Specifically, the system resistance $R_{system}$, of the power supply may be determined by $$R_{system} = \frac{U_{measured} * R_{ref}}{U_{target} - U_{measured}},$$

wherein $U_{target}$ is a pulse height of the excitation voltage signal, $R_{ref}$ is the reference resistance and $U_{measured}$ is a height of the response signal at the start of the rising signal flank, i.e., the ohmic signal portion. The induced signal shape and/or height may be determined, e.g., pre-determined and/or determined during the method. For example, the method may comprise determining a pulse shape and/or height of the excitation voltage signal 114. For example, the output terminal of the signal generator device 118 may be connected to the at least one measurement unit 120 which may be adapted to receive the excitation voltage signal 114 and to determine the pulse height of the excitation voltage signal.

Figure 2:
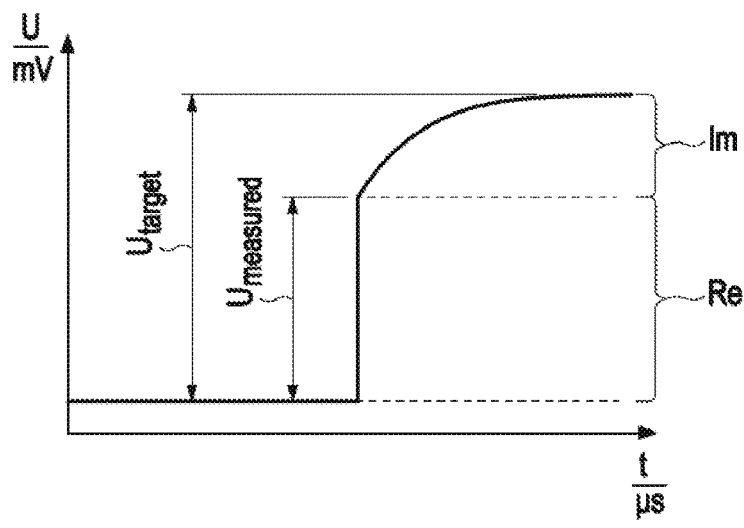
FIG. 2 shows an exemplary measured response signal.

FIG. 2 shows an exemplary measured response signal, in particular voltage U in mV as a function of time t in µs. The response signal as shown in FIG. 2 has a rising signal flank which starts at the voltage value of $U_{measured}$ and rises up to the pulse height of the excitation voltage signal $U_{target}$. In FIG. 2, the ohmic signal portion is denoted with "Re" and the imaginary signal portion is denoted with "Im". The ohmic signal portion and the imaginary signal portion can be separated by analyzing the shape and/or height of the response signal, namely by determining the voltage value at the start of the rising flank.

Figure 3:
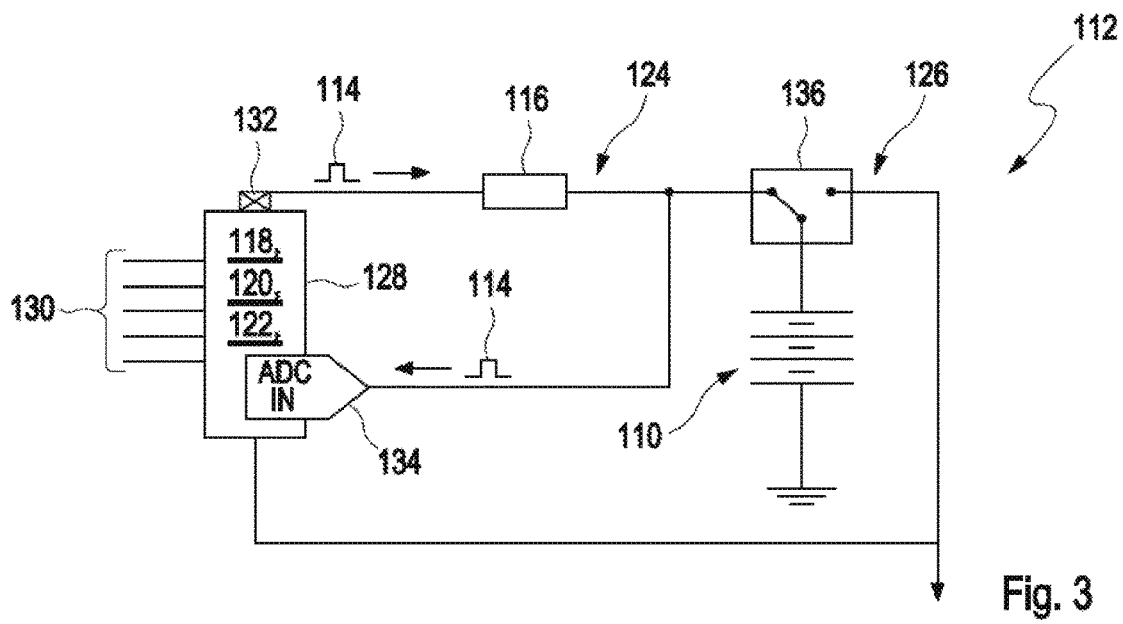
FIG. 3 shows an embodiment of an implementation of a system resistance measurement circuit into the handheld medical device according to the present disclosure.

FIG. 3 shows an embodiment of an implementation of a system resistance measurement circuit 124 into the handheld medical device 112. The handheld medical device 112 may comprise at least one power supply circuit 126 configured for providing power to the at least one element 128 of the handheld medical device 112 and the at least one system resistance measurement circuit 124 configured for determining the system resistance. The system resistance measurement circuit 124 may comprise the power supply 110 and the reference resistor 116 connected to the signal generator device 118 and to the measurement unit 120. In the embodiment shown in FIG. 3, the power supply 110 comprises a battery supply as well as contact resistances, line resistances including possible corrosion on the contact terminals, fuses, which also create resistances and may lead to voltage drops, and inner resistances in the battery itself which lowers the capacity of the battery which can lead to poor performance. In the embodiment shown in FIG. 3, the signal generator device 118 and the measurement unit 120 may be embodied as microprocessor 128 of the handheld medical device 112. The microprocessor and its subsystems may be adapted to control further components 130 of the handheld medical device 112, wherein pins to further components 130 are indicated in FIG. 3. For example, in case the handheld medical device is a meter, the further components 130 may comprise a user interface, blood or sample measurements as well as other functionalities. Reference number 132 is a representation of a general purpose I/O pin on the microprocessor 128.

Figure 8:
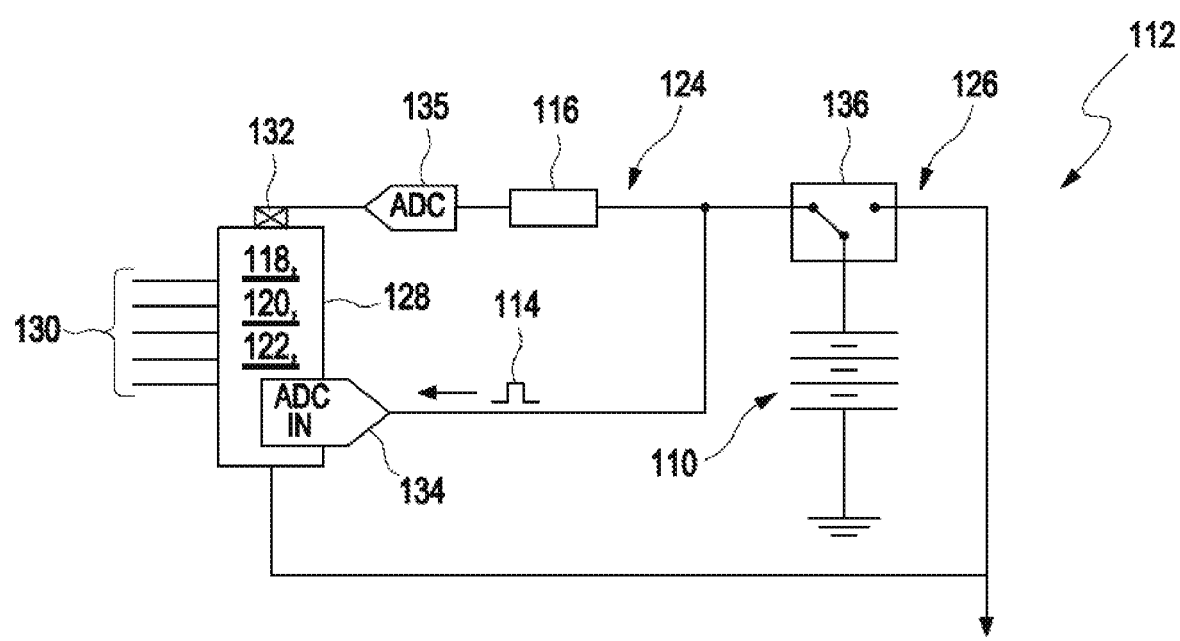
FIG. 8 shows a further embodiment of an implementation of the system resistance measurement circuit into the handheld medical device according to the present disclosure.

The measurement unit 120 may be adapted to detect the response signal generated in response to the excitation voltage signal 114. The measurement unit 120 and the evaluation device 122 may be designed as components of the microprocessor 128. The evaluation device 122 may be configured to evaluate the response. The evaluation device 122 may be or may comprise one or more integrated circuits, such as one or more application-specific integrated circuits (ASICs), and/or one or more data processing devices, such as one or more computers, typically one or more microcomputers and/or microcontrollers. Additional components may be comprised, such as one or more preprocessing devices and/or data acquisition devices, such as one or more devices for receiving and/or preprocessing of the electrode signals, such as one or more converters and/or one or more filters. Further, the evaluation device 122 may comprise one or more data storage devices. Further, as outlined above, the evaluation device 122 may comprise one or more interfaces, such as one or more wireless interfaces and/or one or more wire-bound interfaces. The evaluation device 122 may comprise at least one analog-to-digital convertor (ADC) 134. For example, the ADC 134 may be a 10 to 12 bit ADC. The system resistance measurement circuit 124 may comprise a further ADC 135, shown in FIG. 8. The further ADC 135 may be used for determining the excitation voltage signal $U_{target}$. Therefore, the ADC 135 may be placed in series and between the signal generator device 118 and the reference resistor 116. With respect to description of further elements of FIG. 8, reference is made to FIG. 3.

The handheld medical device 112 may comprise at least one switching element 136. For example, in the embodiment of FIG. 3, the switching element may be at least one field effect transistor (FET) adapted to separate the power supply circuit 126 and the system resistance measurement circuit 124 and/or to switch between the power supply circuit 126 and the system resistance measurement circuit 124. The handheld medical device 112 may be adapted to operate in at least two operational modes. In a first operational mode the handheld medical device 112 may be adapted to determine the system resistance and in a second operational mode the power supply 110 of the handheld medical device 112 may be adapted to provide power to the at least one element 130 of the handheld medical device 112. Using a known reference resistor 116 as found between the I/O pin and the switching element 136, the system resistance can be determined. Advantageously, the required interfaces, the ADC, I/O pin, reference resistor 116, switching element 136 are components available at low costs.

Figure 4:
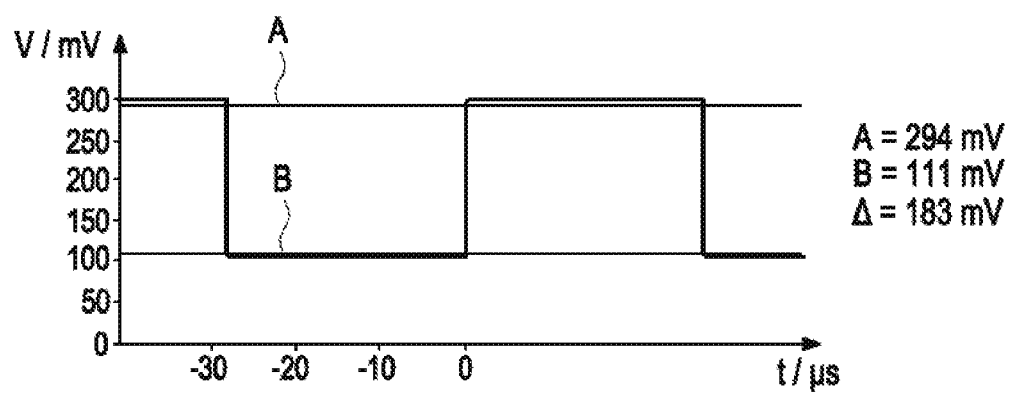
FIGS. 4A to 4F show experimental results, in particular a measured excitation voltage signal (FIG. 4A, 4D), a response signal for a power supply with non-bent contacts (FIG. 4B, 4E) and the response signal for the power supply with bent contacts (FIG. 4C, 4 F)
Figure 4:
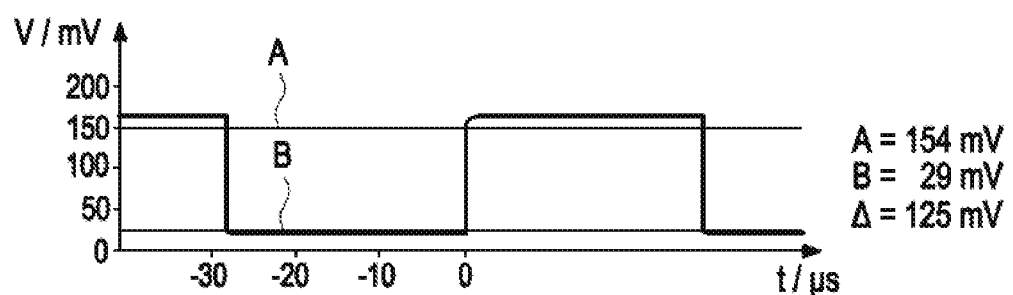
Figure 4:
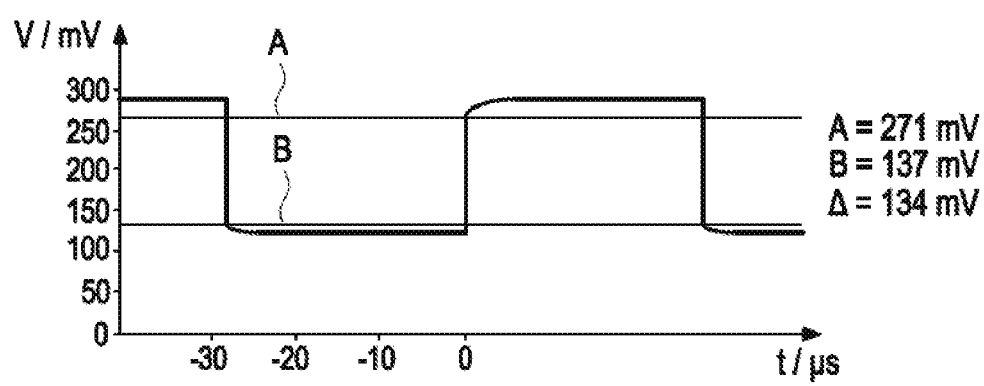
Figure 4D:
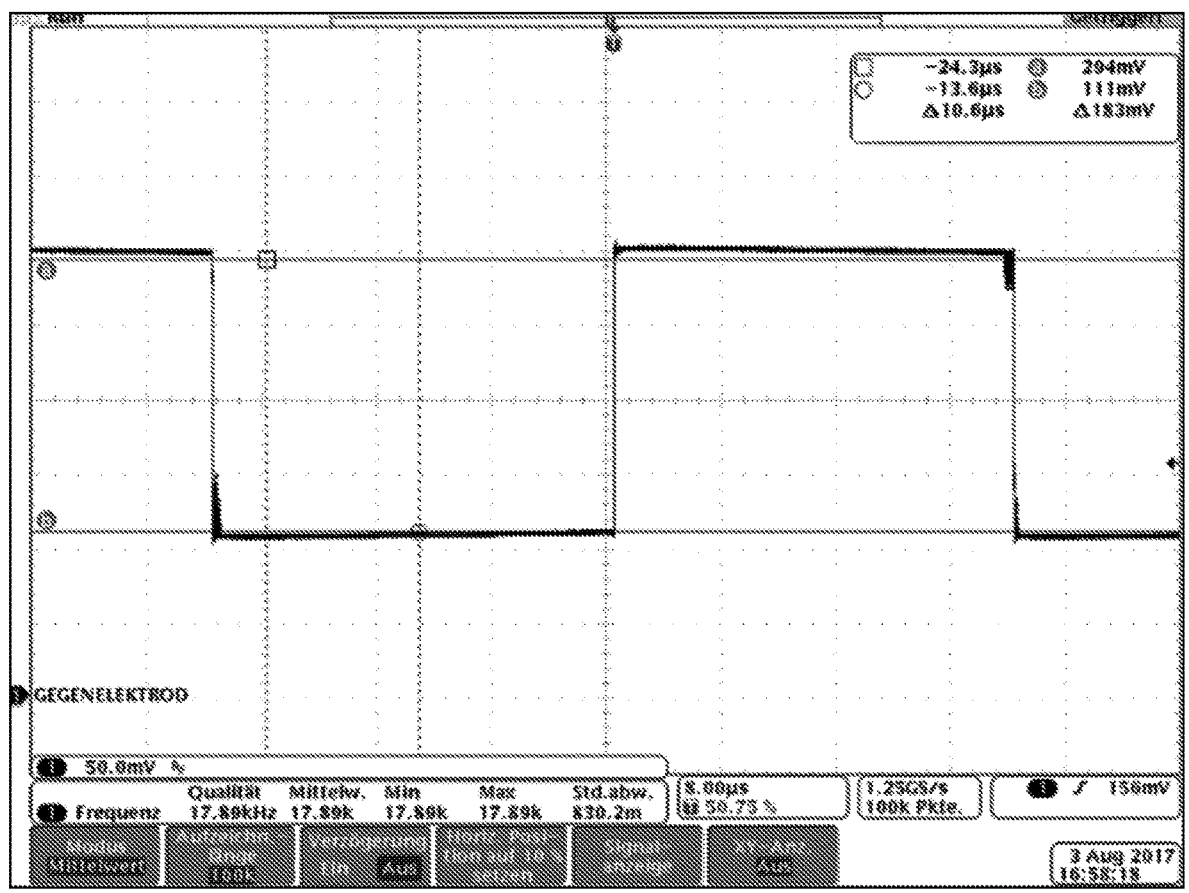
Figure 4E:
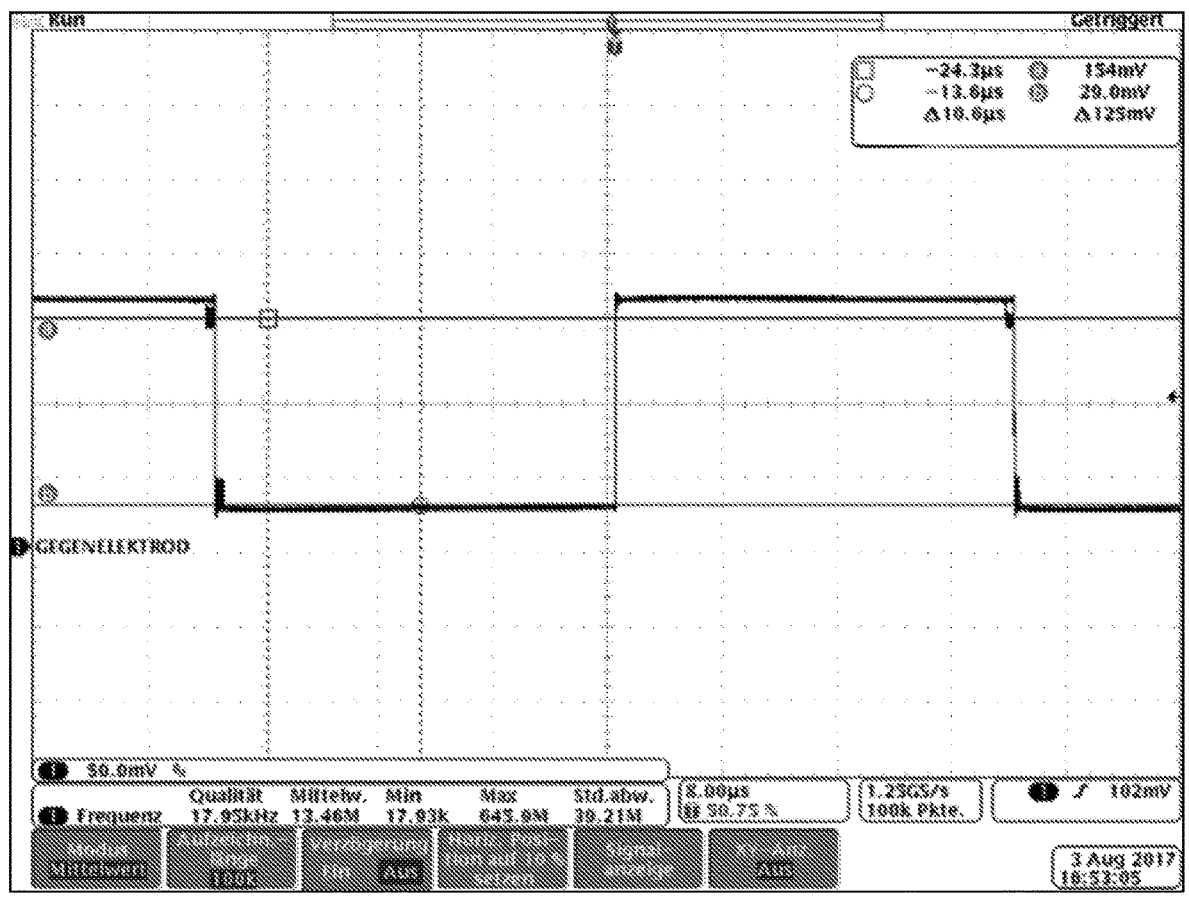
Figure 4F:
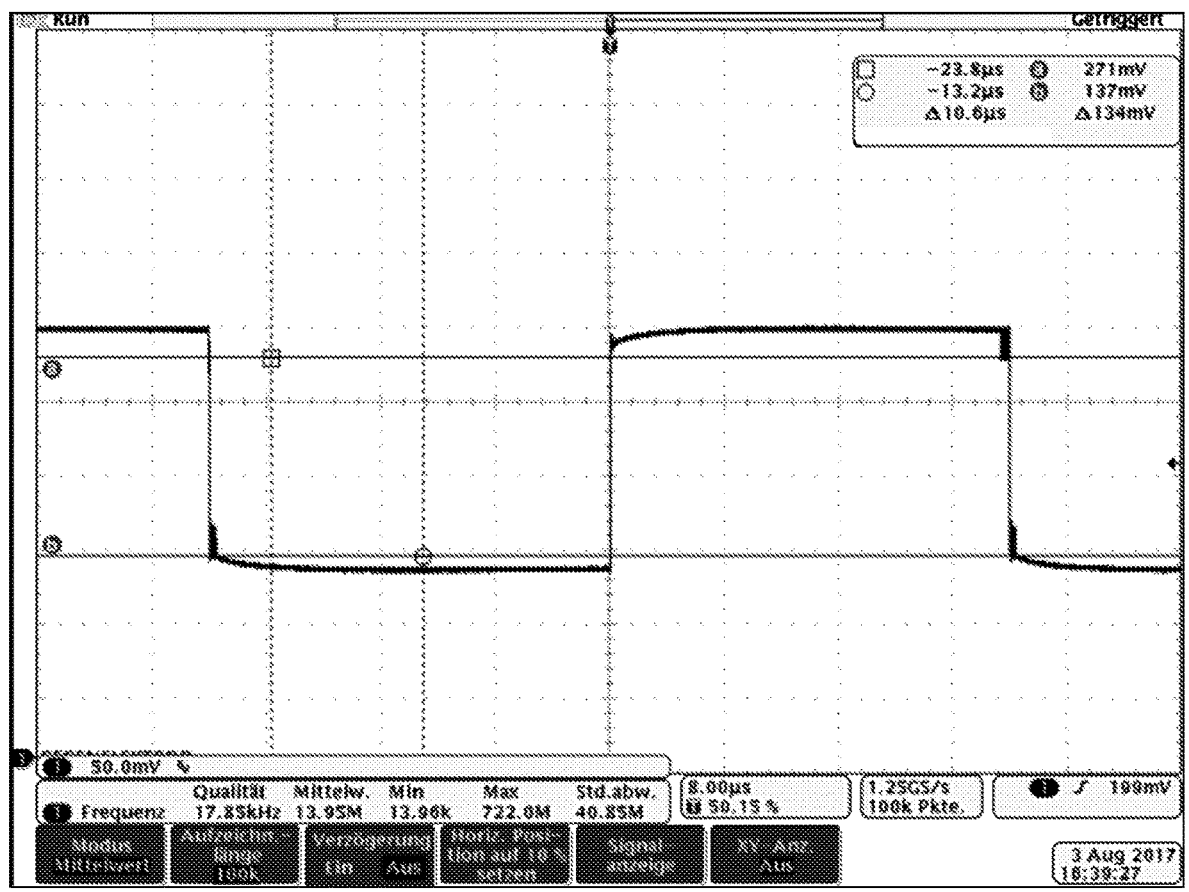

FIGS. 4A to 4F show experimental results determined with a test set up as shown in FIG. 1 with an AAA-battery under test and a reference resistor having a resistance of $R_{ref}$=10Ω. FIGS. 4D to 4F show screenshots of the measurements on an oscilloscope and FIGS. 4A to 4C show corresponding extracted schematic figures, which show quantities for determination of the system resistance. FIGS. 4A and 4D show the voltage curve as a function of time of measured excitation voltage signal 114, in this case a square wave DC voltage signal. A total pulse height of $U_{target}$=183 mV was determined. FIGS. 4B and 4E show the corresponding response signal for an AAA-battery with nonbent contacts. The voltage value at the start of the rising flank was determined to be $U_{measured}$=125 mV. Thus, the system resistance for the power supply with non-bent contacts can be determined to be $$R_{system} = \frac{U_{measured} * R_{ref}}{U_{target} - U_{measured}} = 21.552 \ \Omega.$$

FIGS. 4C and 4F show the response signal for a power supply with the same AAA-battery but with bent contacts simulating corroded or bad contacts or higher inner resistance of the battery which raises the contact resistance and shortens battery life. The voltage value at the start of the rising flank was determined to be $U_{measured}$=134 mV. Thus, the system resistance for the power supply with bent contacts can be determined to be $$R_{system} = \frac{U_{measured} * R_{ref}}{U_{target} - U_{measured}} = 27.552 \ \Omega.$$

In comparison to the system resistance with non-bent contacts an additional system resistance of 5.7Ω was observed which would significantly shorten "lifetime" of the battery. Specifically, even though denoted as "lifetime" of the battery, in fact the battery itself would not be affected, but due to the higher IR drop incurred by the bent contacts, the system being supplied would shut down sooner than expected. Other measurement examples show a true system resistance build up due to increased inner resistance caused by aging, corrosion and the like. Determining of the system resistance of the EDLC may be performed with an analogous test setup. For example, the inner resistance can be measured to characterize the condition of the EDLC during its use.

Figure 5:
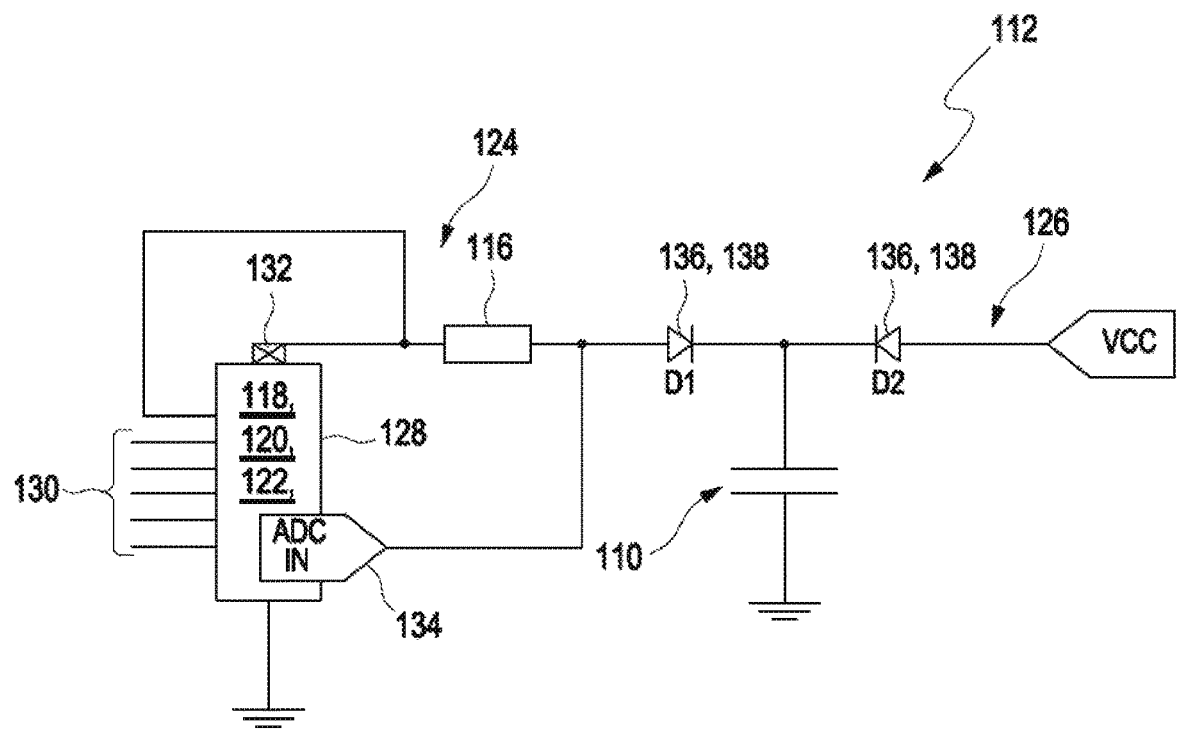
FIG. 5 shows a further embodiment of an implementation of the system resistance measurement circuit into the handheld medical device according to the present disclosure.

FIG. 5 shows a further embodiment of an implementation of the system resistance measurement circuit 124 into the handheld medical device 112. The power supply 110 may comprise at least one battery or at least one EDLC as power source. As in FIG. 3, the handheld device 112 may comprise the system resistance measurement circuit 124 and the one power supply circuit 126. In FIG. 5, the power supply 110 may be implemented as backup power supply in the handheld medical device. The main power supply is denoted as VCC in FIG. 5. The main power supply and the backup power supply are separated by using a diode 138, denoted D2. In the embodiment of FIG. 5, the system resistance measurement circuit 124 and the one power supply circuit 126 may be separated by using a diode 138, denoted D1. With respect to description of further components shown in FIG. 5 reference is made to the description of FIG. 3.

Figure 6:
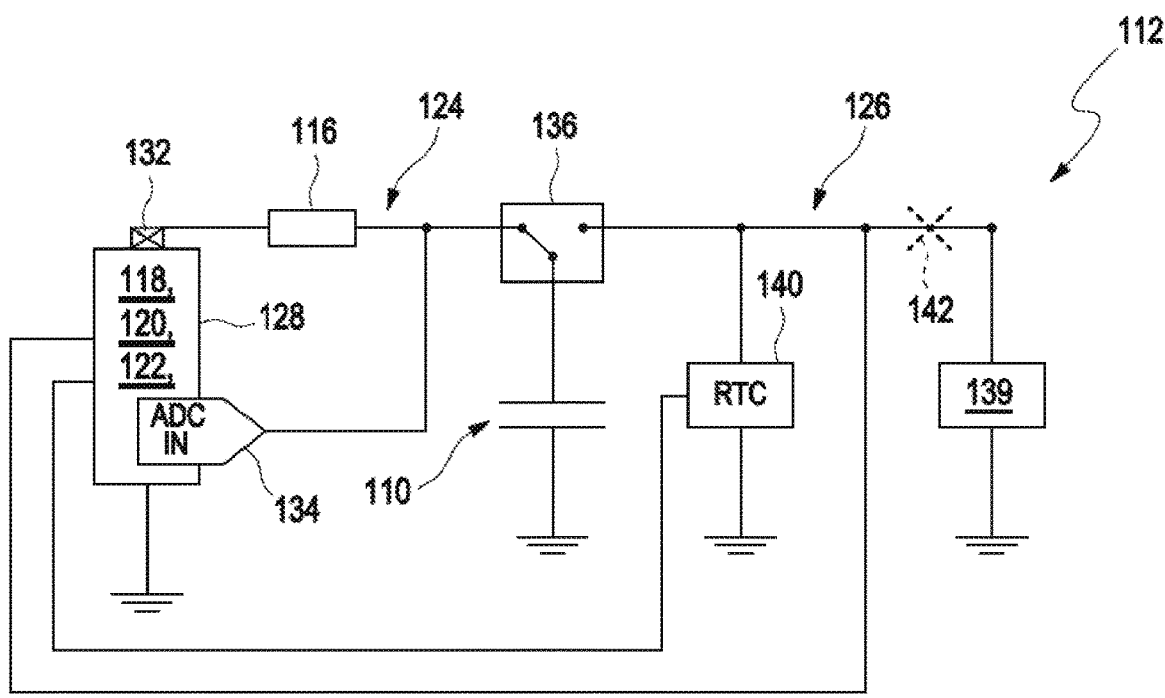
FIG. 6 shows a further embodiment of an implementation of a system resistance measurement circuit into the handheld medical device according to the present disclosure.

FIG. 6 shows a further embodiment of an implementation of a system resistance measurement circuit 124 into the handheld medical device 112. In the embodiment of FIG. 6, the handheld medical device 112 may be embodied as an insulin pump. The handheld medical device may comprise a main power source 139 and the power supply 110 may be embodied as backup power supply. The system resistance measurement circuit 124 in this embodiment may be adapted to determine system resistance of a power supply 110 comprising an Electronic Double Layer Capacitor, which may be used as a power backup during a change of battery, in particular as a backup for a real time clock, or even as a power back up during a battery power failure to alarm the user that there is a problem with the unit, for example, a battery or power failure in an insulin pump which can alarm the user that the pump is not delivering insulin. As in FIG. 3, the handheld medical device 112 may comprise a switching element 136, such as an analog switch or a FET, which is adapted to separate the system resistance measurement circuit 124 from the power supply circuit 126 which may be the standard setting to supply the handheld medical device and the EDLC with energy. Furthermore, the handheld medical device 112 may comprise a real time clock (RTC) 140 which needs constant power in order to keep the clock running. This may be critical, e.g., for insulin pump users who use the clock to time bolus and basal settings on a regular schedule. Failure or drift can lead to wrong timing of these dose administrations. A power failure in which the EDLC would immediately take over the power supply to alarm the user hat there is a problem with the product is indicated with reference number 142 in FIG. 6. As described above, the reference resistor 116 may be used to calculate the height of the response signal through the power supply 110. The system resistance may comprise the complete connection to the EDLC as well as all contact resistances, line resistances including possible corrosion on the contact terminals, other electronic components connected to the EDLC, which also create resistances and lead to voltage drops, and inner resistances in the EDLC itself which lowers the capacity of the EDLC, which can lead to poor performance and short circuits.

Figure 7A:
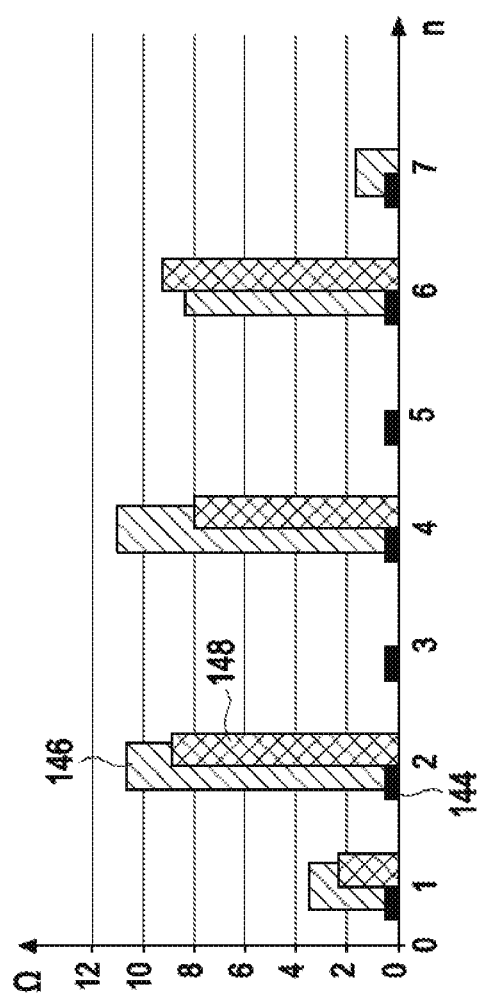
FIGS. 7A and 7B show experimental results of system resistance in Ω for two types of EDLCs at room temperature with ideal EDLC, during heating and after heating.
Figure 7B:
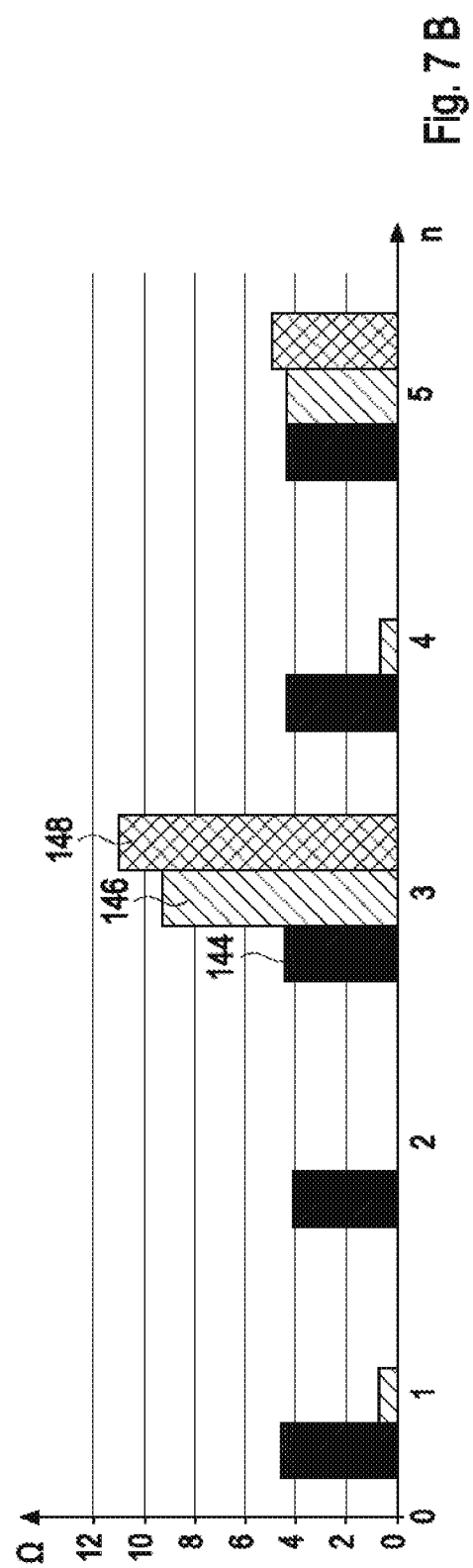

FIGS. 7A and 7B show experimental results of system resistance in Ω for two types of EDLCs at room temperature with an ideal working EDLC (denoted by reference number 144), during heating (denoted by reference number 146) and after heating (denoted by reference number 148). An experimental setup as in FIG. 1 was used, wherein the power supply 110 of FIG. 1 was replaced by two types of EDLCs, the CG 5,5V 1,0F and the XH141, both available from Seiko. The response signals of the EDLCs were measured at room temperature, i.e., 25° C., were then heated to ca 50° C. and were then cooled back to room temperature. FIG. 7A shows the experimental results for seven EDLCs of the type CG 5,5V 1,0F and FIG. 7B shows the experimental results for five EDLCs of the type XH141. In both Figures, the temperature T in ° C. as a function of the EDLC number is shown before, during and after heating. During the first room temperature measurement, see bars 144, it can be observed that the inner resistance from one differs up to 0.5Ω for the CG 5,5V 1,0F (see bars 144 in FIG. 7A) or up to 5Ω for the XH141 (see bars 144 in FIG. 7B). This would indicate an EDLC which is operating within its electrical specification. This type of measurement may be used to qualify the EDLC before installation. When the EDLCs were heated to 50° C. (see bars 146 in FIGS. 7A and 7B), the EDLCs generate a high inner resistance or are no longer acting as a capacitor. The measurements after the heating cycle, see bars 148, at the second room temperature measurement show either a very high remaining inner resistance or the EDLC has been destroyed from heating and no measurement value can be determined. Some of the capacitors after heating do not have a measurement value that can be determined because they have gone into short circuit and are delivering absolutely no more inner resistance or capacitance. A short circuit could cause a quick battery discharge, heating and possibly a dangerous situation for the user, for example, if such energy sources as Lithium polymer batteries are used which can generate enormous amounts of current and heat.

Using pulse measurements on either battery or capacitor sources show many advantages in detecting negative changes at the point of production and during product life. This type of measurement strategy does not require expensive electronic hardware or software support. Using this technique can also reduce risk to the patient which could be caused by a leaky super-cap, bad battery contact points and also a way of detecting capacity.

LIST OF REFERENCE NUMBERS 110 power supply
112 handheld medical device
114 excitation voltage signal
116 reference resistor
118 signal generator device
120 measurement unit
122 evaluation device
124 system resistance measurement circuit
126 power supply circuit
128 microprocessor
130 further components
132 I/O pin
134 ADC
135 Further ADC
136 switching element
138 diode
139 main power source
140 real time clock
142 power failure
144 bar
146 bar
148 bar

What is claimed is:

1. A method for determining system resistance of at least one power supply of a handheld medical device, the method comprising
    a) generating at least one excitation voltage signal, wherein the excitation voltage signal defines a time varying change in voltage having a fast transition DC flank of 20 ns or less;
    b) applying the excitation voltage signal to a power supply via at least one reference resistor having a predetermined or pre-defined resistance value, wherein the reference resistor is electrically connected in series with the power supply at a reference node;
    c) measuring a response signal of the power supply at the reference node, wherein the response signal determines a time varying signal corresponding to an impedance at the reference node;
    d) comparing a shape and height of the excitation voltage signal with a corresponding shape and height of the response signal to determine a difference in the signal flank of the response signal;
    e) determining an ohmic signal portion based on the difference in the signal flank of the response signal; and
    f) determining the system resistance of the power supply from the ohmic signal portion.

2. The method according to the claim 1, wherein the excitation voltage signal defines a square wave signal or a sine wave signal.

3. The method according to claim 1, wherein the excitation voltage signal comprises a non-continuous signal.

4. The method according to claim 1, wherein the reference resistor is connected to at least one electrical contact of the power supply.

5. The method according to claim 1, wherein step d) comprises determining one or both of at least one deviation or difference from an induced signal shape of the excitation voltage signal.

6. The method according to claim 1, wherein the system resistance $R_{system}$ of the power supply is determined by $$R_{system} = \frac{U_{measured} * R_{ref}}{U_{target} - U_{measured}},$$

wherein $U_{target}$ is a pulse height of the excitation voltage signal, $R_{ref}$ is the reference resistance and $U_{measured}$ is a height of the response signal at a start of a rising signal flank of the response signal.

7. The method according to claim 1, wherein the method comprises at least one condition determining step, wherein at least one condition information of the power supply is determined by comparing the determined system resistance of the power supply with at least one predetermined or predefined system resistance value.

8. The method according to claim 1, wherein the method comprises at least one failsafe step, wherein in the failsafe step the determined system resistance of the power supply is compared to at least one predetermined or predefined threshold value.

9. The method according to claim 8, wherein in the failsafe step one or both of a warning is generated if the determined system resistance exceeds the threshold value by a predefined or predetermined value or an abortion of the power supply is initiated if the determined system resistance exceeds the threshold value by a predefined or predetermined value.

10. The method according to claim 3, wherein the non-continuous signal is a pulse.

11. A handheld medical device comprising at least one element, wherein the handheld medical device further comprises:
    at least one power supply for powering said at least one element of the handheld medical device;
    at least one reference resistor having a predetermined or pre-defined reference resistance, wherein the reference resistor is electrically connected in series with the power supply at a reference node;
    at least one signal generator device adapted to generate at least one excitation voltage signal, wherein the excitation voltage signal defines a time varying change in voltage having a fast transition DC flank from 20 ns or less, wherein the signal generator device is adapted to apply the excitation voltage signal to a power supply via the reference resistor;
    at least one measurement unit adapted to measure at least one response signal at the reference node, wherein the at least one response signal determines a time varying signal corresponding to an impedance at the reference node;
    at least one evaluation device adapted to compare a shape and height of the excitation voltage signal with a corresponding shape and height of the at least one response signal to determine a difference in the signal flank of the response signal, to determine an ohmic signal portion based on the difference in the signal flank of the response signal, and to determine a system resistance of the power supply from the ohmic signal portion.

12. The handheld medical device according to claim 11, wherein the handheld medical device is selected from the group consisting of: at least one handheld analytical device; at least one insulin pump; at least one portable sensor for monitoring at least one body function.

13. The handheld medical device according to claim 11, wherein the power supply comprises at least one power source selected from the group consisting of: at least one battery; at least one rechargeable battery, at least one electric double layer capacitor (EDLC).

14. The handheld medical device according to claim 11, wherein the evaluation device comprises at least one microprocessor.

15. The handheld medical device according to claim 11, wherein the evaluation device comprises one or both of at least one analog-to-digital convertor or at least one digital-to-analog convertor.

16. The handheld medical device according to claim 11, wherein the handheld medical device comprises at least one power supply circuit configured for providing power to the at least one element of the handheld medical device and at least one system resistance measurement circuit configured for determining the system resistance, wherein the handheld medical device comprises at least one switching element adapted to separate the power supply circuit and the system resistance measurement circuit.

17. The method according to claim 12, wherein the at least one handheld analytical device comprises at least one handheld meter.

18. The method according to claim 12, wherein the at least one portable sensor for monitoring at least one body function comprises at least one long-term ECG, or an implantable or insertable continuous glucose sensor.

* * * * *